United States Patent [19]
Jain et al.

[11] Patent Number: 5,192,673
[45] Date of Patent: Mar. 9, 1993

[54] MUTANT STRAIN OF C. ACETOBUTYLICUM AND PROCESS FOR MAKING BUTANOL

[75] Inventors: Mahendra K. Jain, Okemos; Daniel Beacom, East Lansing, both of Mich.; Rathin Datta, Chicago, Ill.

[73] Assignee: Michigan Biotechnology Institute, East Lansing, Mich.

[21] Appl. No.: 516,610

[22] Filed: Apr. 30, 1990

[51] Int. Cl.⁵ .......................... C12P 7/16; C12N 1/20
[52] U.S. Cl. ................................. 435/160; 435/252.7; 435/842
[58] Field of Search ...................... 435/160, 252.7, 842

[56] References Cited

U.S. PATENT DOCUMENTS

| | | | |
|---|---|---|---|
| 4,520,104 | 5/1985 | Heady et al. | 435/160 |
| 4,521,516 | 6/1985 | Lemme | 435/252.7 |
| 4,560,658 | 12/1985 | Datta et al. | 435/160 |
| 4,649,112 | 3/1987 | Datta et al. | 435/136 |
| 4,757,010 | 7/1988 | Hermann et al. | 435/252.7 |

OTHER PUBLICATIONS

Lemmel, S. A., "Mutagenesis in *Clostridium acetobutylicum*,", *Biotechnology Letters*, vol. 7, No. 10, pp. 711-716, 1985.

Largier, S. T. et al., "Immobilized Clostridium acetobutylicum P262 Mutants for Solvent Production," *Applied and Environmental Microbiology* 50(2): pp. 477-481 1985.

*Primary Examiner*—David M. Naff
*Assistant Examiner*—Marian C. Knode
*Attorney, Agent, or Firm*—Quarles & Brady

[57] ABSTRACT

A biologically pure asporogenic mutant of *Clostridium acetobutylicum* is produced by growing sporogenic *C. acetobutylicum* ATCC 4259 and treating the parent strain with ethane methane sulfonate. The mutant which as been designated *C. acetobutylicum* ATCC 55025 is useful in an improved ABE fermentation process, and produces high concentrations of butanol and total solvents.

2 Claims, No Drawings

MUTANT STRAIN OF C. ACETOBUTYLICUM AND PROCESS FOR MAKING BUTANOL

FIELD OF THE INVENTION

The present invention relates to a novel mutant strain of *Clostridium acetobutylicum* and a fermentation process for producing butanol using that mutant strain.

BACKGROUND OF THE INVENTION

Diminishing petroleum resources have made the search for alternative fuel and chemical feedstock sources increasingly important. Butanol, in addition to its many uses as a chemical feedstock, is among the alternatives. The acetone/butanol/ethanol (ABE) fermentation, therefore, has received considerable attention in recent years as a prospective process for production of commodity chemicals from biomass.[3,6]

ABE fermentations are biphasic. During the first (acidogenic) phase logarithmic growth is accompanied by acetic and butyric acid production which also causes a drop in pH. In the second (solventogenic) phase growth ceases and the solvents (ABE) are produced concomitant with consumption of already produced acids and further consumption of the carbohydrates. Hydrogen and carbon dioxide are produced throughout the fermentation.

Traditionally, the commercial ABE fermentation was conducted only in a batch mode due to culture instability and spore-forming nature of the organism. Several solvent-yielding fermentation processes using batch or continuous cultures[2,4,7], chemostats with cell recycling[1] or immobilized cell systems[5] have been described. These processes yield butanol, acetone and ethanol in a ratio of 6:3:1[11]. Mixed solvent yields of 29-33% of fermentable carbohydrate have been reported in the literature.[12] A total solvent concentration of about 16-20 g/L and a butanol concentration of 10-12 g/L is generally the limit due to toxicity of the butanol produced.[10]

When *C. acetobutylicum* is grown in a chemostat, different proportions of acids and solvents are produced depending on the dilution rate and the medium composition. In batch fermentation with the spore-forming strain, selectivity and stability is affected by high carbohydrate concentrations and for this reason high carbohydrate containing fermentations have not been practiced.

For a fermentation process to produce butanol and solvents from carbohydrates to be economical, the solvent yield, concentrations and productivity should be as high as possible.

To make the ABE fermentation economically viable, a number of problems must be addressed. The first of these relates to product toxicity. *C. acetobutylicum* is intolerant to high concentrations of butanol,[8] with, as little as 1.3% inhibiting growth and fermentation. However, it is important to note that an increase in the butanol concentration from 1.2% to 2% in the fermentation broth would halve the energy consumption for distillation.[9] The second problem relates to the fermentation of a high level of initial substrate concentration. *C. acetobutylicum* ATCC 4259, will not grow and ferment an initial substrate level higher than 78-80 g/L. Thus, achievable levels of butanol and solvents are limited. An equally important problem with a *C. acetobutylicum* culture is its sporulation which as mentioned earlier is associated with inefficiency of the culture in terms of solvent production. Another problem relates to low productivity. The productivity of the ABE process could be increased by enhancing the fermentation rate of the culture. The organism used for fermentation should have high butyrate uptake activity so that the intermediary compound ends up in butanol and no residual butyrate is left in the fermentation broth. Finally, the instability of the conventional ABE fermentation process is another problem.

BRIEF SUMMARY OF THE INVENTION

It is an object of the present invention to disclose on a mutant microorganism for use in an ABE fermentation. of *C. acetobutylicum*, ATCC (55025) is prepared by treating the parent strain *C. acetobutylicum* (ATCC 4259) with ethyl methane sulfonate. The mutant is asporogenic, has a high butyrate uptake rate, a good tolerance to increased initial substrate levels and butanol produced, and that it produces high levels of solvents in high yield when used in an ABE fermentation process. The mutant has been deposited with American Type Culture Collection and assigned ATCC 55025.

We also have discovered that high butanol and solvent concentrations can be obtained by using this mutant in an improved fermentation process which basically comprises an initial continuous fermentation stage or stages followed by batch fermentation(s) to completion. The improved process using the mutant results in butanol and solvent yields of between 22 to 38%, and permits an increase in initial substrate concentration which helps achieve increased levels of butanol and total solvents. The mutant strain also has in an unexpectedly high uptake of butyrate which results in high concentration of butanol in the fermentation broth with low residual butyrate. The increased concentration facilitates recovery of the butanol, thereby reducing the energy and costs of distillation.

Other advantages and objects of the invention will be apparent to those skilled in the art from the description of the asporogenic strain, process and the examples.

DESCRIPTION OF PREFERRED EMBODIMENT

In the preferred practice of the invention, a mutant strain *C. acetobutylicum* ATCC 55025, is prepared by growing a culture of *C. acetobutylicum* ATCC 4259 at about pH 4.9 to about 5.6 at about 33 to about 38° C for about 9 to about 18 hours, treating the cells with aqueous ethyl methane sulfonate, growing the treated cells anaerobically and selecting and isolating the asporogenic cells. The asporogenic strain has an increased tolerance to the high initial substrate levels, butanol and solvent levels, and has high butyrate uptake rate.

In the preferred method of the invention, the mutant is employed in a process configuration which comprises first a three-stage continuous fermentation at about 36° C followed by batch fermentation(s) of the fermentation broth from second or subsequent stages of continuous fermentation.

The practice of the invention is illustrated by the examples in which the following materials and methods were used:

Organisms

*Clostridium acetobutylicum* parent strain (ATCC 4259) was obtained from American Type Culture Collection, Rockville, Md. while the mutant strain E604 of *C. acetobutylicum* (ATCC 55025) was prepared at Michigan Biotechnology Institute, Lansing, Mich.

Growth and Fermentation Media

The media for growth unless otherwise stated contained starch hydrolysate (Maltrin M-100) 60 g/L, commercially available corn steep liquor, 10 g/L (d.b.), and corn gluten (Prarie Gold), 10 g/L d.s.; pH was adjusted to 5.4 with NaOH. Fifty ml of medium reduced with 0.025% cysteine-sulfide was inoculated from a fresh stock culture and incubated at 36±1° C. anaerobically for 12 hours. Agar medium was made by supplementing the growth medium with Bacto-agar (Difco, Ann Arbor, Mich.) at 2.0%.

Mutant colonies were picked up in tubes containing CAB medium which contained (g/L): glucose, 30; yeast extract, 4; tryptone, 1; $KH_2PO_4$, 0.7; $K_2HPO_4$. DL-asparagine, 0.5; $MgSO_4.7H_2O$. 0.1; $MnSO_4.H_2O$ 1.0; $FeSO_4.7H_2O$, 0.015; NaCl,0.1; and resazurin, (0.2%), 1 ml. The pH was adjusted to 5.4 and after autoclaving the media tubes were reduced with cysteine-sulfide (2.5%) @ 0.1 ml/10 ml.

Media for fermentation contained:

| Starch hydrolysate (Maltodextrin M-100) | 50–60 g/L | 80 g/L | 100 g/L |
|---|---|---|---|
| Corn Steep Liquor, CSL (d.b.) | 7.5 g/L | 10 g/L | 11.3 g/L |
| Gluten (d.b.) | 7.5 g/L | 10 g/L | 11.3 g/L |
| $FeSO_4$ | 5 ppm | 5 ppm | 5 ppm |

The pH of the medium was adjusted to 5.2 with concentrated NaOH before autoclaving. The gluten and CSL were autoclaved separately and added later. All the media were boiled and gassed with $N_2$ prior to fermentation.

Butyrate Uptake Studies

Butyrate uptake experiments were carried out in 58 ml serum vials (Wheaton, Millville, N.J.). These vials were made anaerobic by repeated evacuation and flushing with N2 gas. Twenty ml effluent from stage 2 fermentor was anaerobically transferred to the serum vial, to which was then added a desired concentration of sodium butyrate solution before incubation. Samples were withdrawn at different time intervals. Controls without addition of butyrate were also kept.

Quantitative Analysis of Substrates and Products

Carbohydrate substrate was analyzed as dextrose equivalent using YSI analyzer after treatment with glucoamylase and α-amylase. Soluble fermentation products were analyzed using GC fitted with chromosorb column with injector, column and detector temperature being 230, 170 and 250° C., respectively.

EXAMPLE 1

Mutagenesis

The parent strain of C. acetobutylicum (ATCC 4259) was grown in the media containing 60 g/L maltrin (M-100), 10 g/L corn gluten, and 10 g/L corn steep liquor (d.b.) pH was adjusted to 5.3 and after autoclaving at 121° C. for 25 min cysteine-sulfide was added at 0.20 ml/10 ml. When the culture was in active state after 12 h growth at 37° C., 5 ml of it was treated with 0.2 ml of 1:1 diluted aqueous ethyl methane sulfonate (EMS) solution. A drop of titanium (Ti-NTA) solution was added to keep the reduced conditions in the tube. The culture medium inoculated with the EMS mutagen was incubated at 37° C. for 60 min. At the end of incubation, the cells were pelleted by centrifugation at 3000×g for 10 min. The supernatant containing EMS was removed by syringe and the cells were washed twice with the reduced media. Finally, the pellet was resuspended in 9 ml of reduced media and the culture was incubated at 37° C. for 24 h. At the end of incubation, the cells were centrifuged at 3000×g for 10 min and the pellet was resuspended in the fresh media. After another 24 h growth at 37° C., a tube containing fresh media was inoculated with this culture using a 5% inoculum. After 12 h of growth, the culture was plated on the same media containing 2% agar in an anaerobic glove box. The plates were incubated anaerobically under a blanket of nitrogen gas. After 4 days of growth at 37° C. the colonies were picked by sterile toothpicks and placed into tubes containing CAB media. After growth, the cells were observed for sporulation and the asporogenic cultures were selected and isolated. The mutant ATCC 55025 was further streaked onto agar plates of CAB media to obtain a pure culture.

EXAMPLE 2

Butanol Tolerance

The ability of the parent strain and the mutant to tolerate and grow in presence of various levels of end product butanol was examined in 58 ml serum vials under batch conditions. Various levels of butanol ranging from 1–11 g/L was added to the medium in vials (initial carbohydrate, 10 g/L) before inoculation and the vials were incubated at 36° C. After 35 hours of incubation, growth was examined by measuring absorbance at 660 nm and by analyzing production of butyrate in the culture broth.

TABLE 1

Butanol tolerance of parent strain (ATCC 4259) and mutant strain (ATCC 55025) of C. acetobutylicum

| Initial Butanol g/L | ATCC 4259 | | ATCC 55025 | |
|---|---|---|---|---|
| | Growth $A_{660\ nm}$ | Butyrate Production g/L | Growth $A_{660\ nm}$ | Butyrate Production g/L |
| 0 | 0.8 | 1.3 | 1.1 | 1.1 |
| 2.75 | 0.6 | 1.0 | 1.1 | 1.1 |
| 5.2 | 0.0 | 0.1 | 1.1 | 1.1 |
| 6.9 | 0.0 | 0.1 | 1.0 | 1.0 |
| 8.9 | 0.0 | 0.1 | 0.9 | 0.7 |
| 11.4 | 0.0 | 0.0 | 0.6 | 0.5 |

Results presented in Table 1 clearly indicate that growth initiation of the parent strain was inhibited at initial butanol level above 5.0 g/L. However, the growth initiation of the mutant strain was not affected up to an initial butanol level of about 11.4 g/L. Even at such high concentrations of butanol only the growth rate was affected but not the ability of the mutant to initiate the growth and ferment the substrate. These results indicate that the mutant strain has more tolerance to the end product butanol than the parent strain.

EXAMPLE 3

Batch Fermentation

The comparative results obtained when batch fermentations were run using the parent and mutant strain of C. acetobutylicum are shown in Table 2. In the batch fermentations the initial substrate concentration was approximately 60 g/L, the pH was controlled between 5.0 and 5.2, the fermentation temperature was 36° C. and agitation was set at 200 rpm. The fermentations were run in a 2-liter fermentor with 1-liter working volumes.

TABLE 2

Comparison of parent and mutant strains of *C. acetobutylicum* (Batch fermentation)

| Strain | Substrate Consumption Rate g/L hr | Actual Final Butanol g/L | Butanol Productivity g/L hr | Butanol Yield (wt %) |
|---|---|---|---|---|
| Parent (ATCC 4259) | 0.79 | 10.6 | 0.17 | 21.3 |
| Mutant (ATCC 55025) | 1.45 | 13.0 | 0.33 | 22.7 |

The fermentation with mutant strain ATCC 55025 was completed much earlier than parent strain. A substrate consumption rate of 1.45 g/L hr was obtained for mutant strain which was nearly twice the rate of parent strain. Similarly, butanol productivity rates by mutant strain were also almost twice (0.33 vs 0.17 g/L hr) in comparison to parent strain. Actual final butanol concentration in the fermentation broth of the parent strain was 10.6 g/L while in that of mutant it was 13.0 g/L. Butanol yield by mutant was also higher than parent strain.

The results indicate that under the same batch fermentation conditions the mutant strain unexpectedly shows a very active fermentation in terms of increased substrate consumption and butanol productivity rates.

EXAMPLE 4

Continuous Fermentation

The mutant strain and the parent strain were also compared in the multistage continuous fermentation configuration in terms of butanol and total solvent concentrations and solvent productivity rates. The fermentation process equipment consisted of three continuous fermentors in series with respective dilution rates of 0.25, 0.135 and 0.135 h$^{-1}$ for stage 1, stage 2 and stage 3. Stage 1 continuous fermentor was a New Brunswick Multigen fermentor with 400 ml working volume. The pH was controlled at 5.1±1° C. with 4N NaOH at 200 rpm agitation. Stage 2 and 3 were Multigen fermentors with 1-liter working volumes. The temperatures in all the stages were maintained at 36° C. The pH was controlled only in the first stage. The fermentation in stage 2 and 3 were self-buffering and required no pH control. Agitation was set at 200 rpm.

The results presented in Table 3 represent the average of at least 4 observations after the steady-state. Only acids were produced in the stage 1 with no detectable production of butanol, acetone or ethanol. However, stage 2 data show that butanol and total solvent concentrations produced by mutant were higher by 41–45% and this was repeated in stage 3. The solvent productivity rates in stage 2 (0.90 vs 0.64 g/L hr, mutant vs parent strain) as well as stage 3 (0.96 vs 0.71 g/L hr, mutant vs parent strain) also show that mutant strain has better fermentation rate. The results indicate that the mutant strain also performs better in a multistage continuous fermentation system when compared with parent strain in terms of butanol and total solvents concentrations and solvent productivity rates.

TABLE 3

Comparative Performance of Parent (ATCC 4259) and Mutant (ATCC 55025) Strain of *C. acetobutylicum* (Multistage, Continuous Fermentation of Steady-State)

| Fermentation Stage | Butanol Production (g/L) ATCC 4259 | Butanol Production (g/L) ATCC 55025 | Solvent Production (g/L) ATCC 4259 | Solvent Production (g/L) ATCC 55025 | Solvent Productivity (g/L hr) ATCC 4259 | Solvent Productivity (g/L hr) ATCC 55025 |
|---|---|---|---|---|---|---|
| 1 | 0 | 0 | 0 | 0 | 0 | 0 |
| 2 | 4.7 | 6.8 | 7.3 | 10.3 | 0.63 | 0.90 |
| 3 | 8.7 | 11.6 | 13.3 | 18.0 | 0.70 | 0.95 |
| Dilution Rate Rate (−1) | Stage 1 0.25 | | Stage 2 0.135 | | Stage 3 0.135 | |
| pH: | 5.1 ± 1° C. | | Uncontrolled | | Uncontrolled | |
| Temperature (°C.) | 36 | | 36 | | 36 | |

EXAMPLE 5

Butyrate Uptake

The butyrate uptake rates of parent and mutant strain were compared in 158 ml serum vials by supplementing additional butyrate (approximately 4.7 g/L) to stage two effluent of a three stage continuous system and incubating at 30° C. After incubation for 24 h, the culture broth was analyzed for butyrate, butanol, acetone and ethanol.

The results presented in Table 4 indicate that the mutant has about 27% higher butyrate uptake rate (0.33 vs 0.26 g/L hr) in comparison to parent strain. The butyrate conversion efficiency for the mutant was also higher (97.5%) as compared to parent strain (86.6%). The data indicate that mutant strain has a much better butyrate uptake rate and butyrate conversion efficiency than the parent strain. Also the repetitive fermentation runs with the mutant showed only negligible residual butyrate level (about 1/10th or less in comparison to parent strain) in the fermentation broth. This also indicates that butyrate uptake rate of the mutant strain was much higher than the parent strain.

TABLE 4

Comparison of Parent and Mutant Strains of *C. acetobutylicum* for Butyrate Uptake Using Stage Two Broth in Three Stage Continuous Process at Steady-State

| Parameter | Parent Strain ATCC 4259 | Mutant Strain ATCC 55025 |
|---|---|---|
| Butanol (g/L) | 13.9 | 17.6 |
| Total Solvents (g/L) | 18.8 | 25.3 |
| Solvent Production Rate (g/L hr) | 0.53 | 0.71 |
| Butyrate Uptake Rate (g/L hr)* | 0.26 | 0.33 |
| Butyrate Conversion Efficiency (%)** | 86.6 | 97.5 |

*Butyrate was added at the concentration of 4.7 ± 0.6 g/L in the stage two broth contained in a vial and incubated for 24 hours at 30° C.
**Calculations based on butyrate conversion in 24 hours in vials

EXAMPLE 6

Substrate Tolerance

The parent and mutant strains were compared in relation to their ability to initiate growth at, and ferment, high initial substrate concentration. The comparison was made in the multistage continuous fermentation process followed by batch fermentation of second and third stage fermentation broth to completion. The initial substrate concentration was 97 g/L.

The parent strain was not able to initiate growth and ferment substrate when the substrate concentrations was 97 g/L. In contrast, the mutant strain initiated growth and fermented such a high substrate concentration. The results obtained are presented in Tables 5 and 6.

At steady-state, stage three showed 3.8 g/L acids and 16.2 g/L total solvents (Table 5) in a residence time of 19 hours during which a total of about 58 g/L substrate was consumed. The results of batch fermentation of stage three broth presented in Table 6 show that a very high concentration of butanol (approximately 20 g/L) and total solvents (about 30 g/L) can be achieved.

TABLE 5

Three Stage Continuous Fermentation by C. acetobutylicum mutant at Elevated Substrate Level Steady-State).

| Stage | Total Carbohydrates as glucose g/L | Fermentation Products (g/L) | | | | |
|---|---|---|---|---|---|---|
| | | Acetic Acid | Butyric Acid | Acetone | Butanol | Ethanol |
| Feed | 97.0 | — | — | — | — | — |
| Stage One | 85.2 | 1.1 | 1.9 | — | 0.1 | — |
| Stage Two | 57.0 | 1.6 | 2.5 | 2.3 | 5.9 | 0.6 |
| Stage Three | 39.0 | 1.7 | 2.1 | 4.6 | 10.8 | 0.8 |

TABLE 6

Batch Fermentation of Stage Two and Three Broth of Process with Elevated Substrate Level for 48 h.

| | Stage Two | Stage Three |
|---|---|---|
| Products (g/L) | | |
| Acetic Acid | 1.8 | 1.7 |
| Butyric Acid | 0.2 | 0.1 |
| Acetone | 6.9 | 8.4 |
| Butanol | 19.6 | 20.2 |
| Ethanol | 1.4 | 1.5 |
| Total Solvents | 27.9 | 30.1 |
| Substrate (g/L) Residual Carbohydrate Substrate (g/L) | 12.2 | 10.0 |

These results show that the mutant strain is better than the parent strain in tolerance to high substrate concentrations. The mutant strain under the multistage continuous fermentation coupled to batch fermentation and high substrate concentrations has produced butanol (20 g/L) and total solvents (30 g/L) in very high concentrations.

EXAMPLE 7

Comparison of Parent and Mutant Strains

Side by side comparison of parent and mutant strain under identical conditions, i.e. vials, batch fermentations, continuous fermentations, multistage continuous - batch fermentations, high substrate concentration, has shown that the asporogenic mutant strain is an improved and better strain than the parent strain. The key results obtained under examples 1 to 6 are summarized in Table 7.

TABLE 7

Summary comparison of parent and mutant strain of C. acetobutylicum

| Parameters | Parent Strain (ATCC 4259) | Mutant Strain (ATCC 55025) |
|---|---|---|
| Sporulation | + | — |
| Maximum Substrate Tolerance (g/L) | 78.5 | 97.0 |
| Maximum Butanol | 16.7 | 20.2 |

TABLE 7-continued

Summary comparison of parent and mutant strain of C. acetobutylicum

| Parameters | Parent Strain (ATCC 4259) | Mutant Strain (ATCC 55025) |
|---|---|---|
| Production (g/L) | | |
| Maximum Total Solvent Production (g/L) | 25.3 | 30.1 |
| Butyrate Uptake Rate (g/L hr) | 0.26 | 0.33 |
| Butyrate Conversion Efficiency (%) | 86.6 | 97.5 |

The results show that the mutant strain of C. acetobutylicum ATCC 55025 is much better than parent strain; it can tolerate a very high level of substrate (greater than 95 g/L), butanol, and total solvent concentrations; it can produce a high concentration of butanol (greater than 20 g/L) thus cost of recovery could be reduced; it can produce a high concentration of solvents (greater than 30 g/L); it has a higher rate of butyrate uptake; it has a high substrate consumption rate; it has shown high solvent productivity; and it is stable in batch as well as multistage continuous fermentation processes.

REFERENCES

1. Afschar, A. S., H. Biebl, K. Schaller, and K. Schugerl. 1985. Production of acetone and butanol by *Clostridium acetobutylicum* in continuous culture with cell recycle. Eur. J. Appl. Microbiol. Biotechnol. 22:394–398.
2. Bahl, H., W. Andersch, and G. Gottschalk. 1982. Continuous production of acetone and butanol by *C. acetobutylicum* in a two-stage phosphate limited chemostat. Eur. J. Appl. Microbiol. Biotechnol. 15:201–205.
3. Gibbs, D. F. 1983. The rise and fall (. . . and rise?) of acetone/butanol fermentations. Trends Biotechnol. 1:12–15.
4. Gottschal, J. C. and G. Morris. 1982. Continuous production of acetone and butanol by *Clostridium acetobutylicum* growing in turbidostat culture. Biotechnol. Lett. 4:477–482.
5. Haggstrom, L. and S. O. Enfors. 1982. Continuous production of butanol with immobilized cells of Clostridium acetobutylicum. Appl. Biochem. Biotechnol. 7:35–37.
6. Jones, D. T. and D. R. Woods. 1986. Acetone-butanol fermentation revisited. Microbiol. Rev. 50:484–524.
7. Kim, B. H., P. Bellows, R. Datta and J. G. Zeikus. 1984. Control of carbon and electron flow in *Clostridium acetobutylicum* fermentation: utilization of carbon monoxide to inhibit hydrogen production and to enhance butanol yields. Appl. Environ. Microbiol. 48:764–770.
8. Linden, J. C. and A. R. Moreira. 1983. Anaerobic production of chemicals. In "Biological Basis for New Developments in Biotechnology", eds. A. Hollander, A. I. Laskin and P. Rogers, p. 377. Plenum Pub. Co., New York
9. Linden J. C., Moreira, A. R. and T. G. Lenz. 1986. Acetone and Butanol. In "Comprehensive Biotechnology" ed. M. Moo Young, vol. 3, The Practice of Biotechnology: Current Commodity Products, eds. H. W. Blanch, S. Drew and D. I. C. Wang, p. 915–931. Pergamon Press, Oxford, England.
10. Moreira, A. R., A. C. Ulmer and J. C. Linden. 1981. Butanol toxicity in the butylic fermentation. Biotechnology and Bioengineering Symposium. 11:567–579.
11. Prescott, S. C. and C. G. Dunn. 1959. The acetone butanol fermentation, p. 250–284. In S. C. Prescott and C. G. Dunn (ed.), Industrial Microbiology, 3rd ed. McGraw Hill Book Co., New York.
12. Underkofler, L. A. and R. Hickey, Eds. Chemical Publishing Co., New York, 1954. Chap. 11, pp. 347–390.

We claim:

1. A method of producing butanol which comprises anaerobically culturing a biologically pure culture of *Clostridium acetobutylicum* ATCC 55025 in a nutrient medium with assimilable sources of carbon, nitrogen, and inorganic substances and then recovering the butanol.

2. A biologically pure culture of *clostridium acetobutylicum* ATCC 55025.

* * * * *